United States Patent
Hung

(10) Patent No.: US 8,052,422 B2
(45) Date of Patent: Nov. 8, 2011

(54) DENTAL IMPLANT

(76) Inventor: William Y. S. Hung, Rancho Cucamonga, CA (US)

(*) Notice: Subject to any disclaimer, the term of this patent is extended or adjusted under 35 U.S.C. 154(b) by 331 days.

(21) Appl. No.: 12/231,175

(22) Filed: Aug. 29, 2008

(65) Prior Publication Data
US 2010/0055643 A1    Mar. 4, 2010

(51) Int. Cl.
*A61C 8/00* (2006.01)
(52) U.S. Cl. .................................... 433/174
(58) Field of Classification Search .......... 433/172–176, 433/201.1; 411/419, 422, 424
See application file for complete search history.

(56) References Cited

U.S. PATENT DOCUMENTS

| | | | |
|---|---|---|---|
| 5,087,199 A * | 2/1992 | Lazarof | 433/173 |
| 2004/0006346 A1* | 1/2004 | Holmen et al. | 606/73 |
| 2005/0164146 A1* | 7/2005 | Cantor | 433/173 |
| 2007/0037123 A1* | 2/2007 | Mansueto et al. | 433/173 |

* cited by examiner

Primary Examiner — Cris L Rodriguez
Assistant Examiner — Edward Moran
(74) Attorney, Agent, or Firm — Raymond Y. Chan; David and Raymond Patent Firm

(57) ABSTRACT

A dental implant includes a dental implant body which is a cylinder body having a first end and a second end, an asymmetric thread being provided around the dental implant body, an apex lock being formed at the first end for inserting into a sinus of a desired position, and an endomaximum lock being provided at the second end for integrally connected with an abutment through a bolt. The apex lock is a space indented in the first end for enabling new grown bone of the sinus extending into the apex lock to provide a locking mechanism to ensure integration between the dental implant and the bone. The endomaximum lock has a lock cavity having a lock opening at the second end for receiving a root of the abutment therein.

13 Claims, 5 Drawing Sheets

DENTAL IMPLANT

BACKGROUND OF THE PRESENT INVENTION

1. Field of Invention

The present invention relates to dental implants, and particularly to (1) a dental implant having an (a) apex lock and (b) trepanelevation for better osseous integration and sinus lift (2) an endomaximum lock design, water crystal like (6 engaging slots), for maximum friction/stability, (3) ferrulobrace for additional stability/seating. (4) Unsymmetrical (sharp) threads providing self drilling effect/reduce resistance of bone—also called Drill Implant.

2. Description of Related Arts

A dental implant is an artificial tooth root replacement and is used in prosthetic dentistry to support restorations that resemble a tooth or group of teeth. Millions of implants have been placed to replace missing teeth per year in the 20 years. However, there are still many problems regarding safe, patient comfort, prognosis, esthetics, and cost which results in only less than 3% of dentists provide this service to patients and less than 5% of the patients who really need dental implants service receiving this service.

Therefore, design of a new dental implant become very important to (1) shorten the period of osseousintergration (2) reduce the time of treatment (3) reduce the cost of implant dentistry (4) increase successful rate, (5) improve patient comfort, (6) improve esthetics and function. The more important issue is to encourage dentists and dental specialists to provide this services to their patients by developing a new implant design, which can increase primary stability, reduce surgical trauma to patients, shorten surgical time/time for restoration, increase quantity/quality of osseointegration, avoid additional bone graft procedures, increase stability and surface contact between implant, abutment and screw to avoid post restoration failure and reduce the issue of technique sensitive.

SUMMARY OF THE PRESENT INVENTION

A main object of the present invention is to provide a dental implant which is increasing quantity and quality of osseointegration.

Another object of the present invention is to provide a dental implant which is convenient to be placed and reduce the issue of technique sensitive.

Another object of the present invention is to provide a dental implant which gains maximum primary stability.

Another object of the present invention is to provide a dental implant to increase the preservation of bone.

Another object of the present invention is to provide a dental implant to prevent implant rotation after operation.

Another object of the present invention is to provide a dental implant to prevent the screw loose of the abutment, which is a major issue of post treatment failure.

Another object of the present invention is to provide a dental implant to increase the successful rate of operation, to avoid multiple surgeries and to improve esthetics/function.

Another object of the present invention is to shorten the time of surgery, restoration, and treatment period.

Accordingly, in order to accomplish the above objects, the present invention provides a dental implant, comprising:

a dental implant body;

an apex for locking on the apical port of the implant;

a Sino lift and/or trepan elevation on apical end of the implant;

an endomaximum lock inside the dental implant body for maximizing friction between abutment and the implant;

an asymmetric thread on the outer wall of the middle portion and spiral shaping edge on the outer wall of apical portion of the dental implant body; and ferrulobracing design to provide additional seating/stability and esthetics.

These and other objectives, features, and advantages of the present invention will become apparent from the following detailed description, the accompanying drawings, and the appended claims.

DETAILED DESCRIPTION OF THE PREFERRED EMBODIMENT

Figure 1:
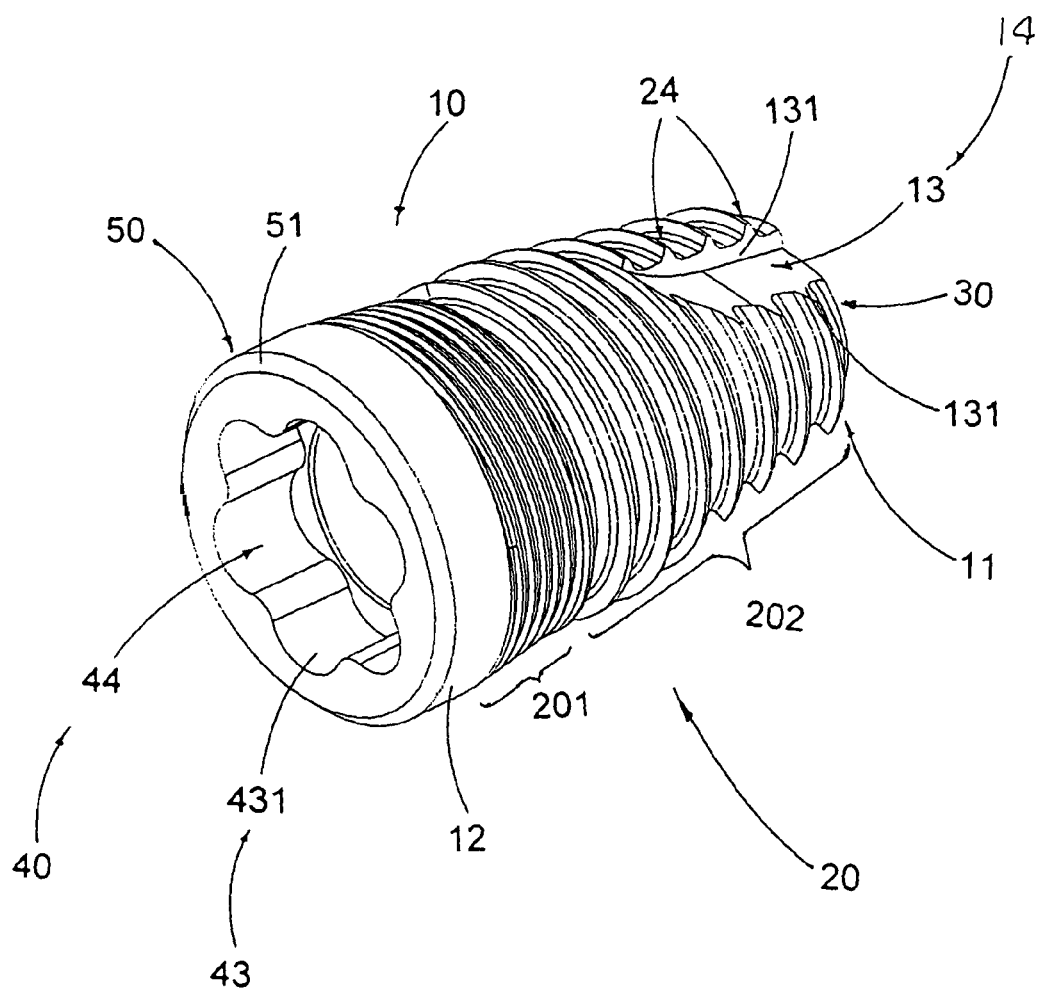
FIG. 1 is a perspective view of a dental implant according a preferred embodiment of the present invention.
Figure 2:
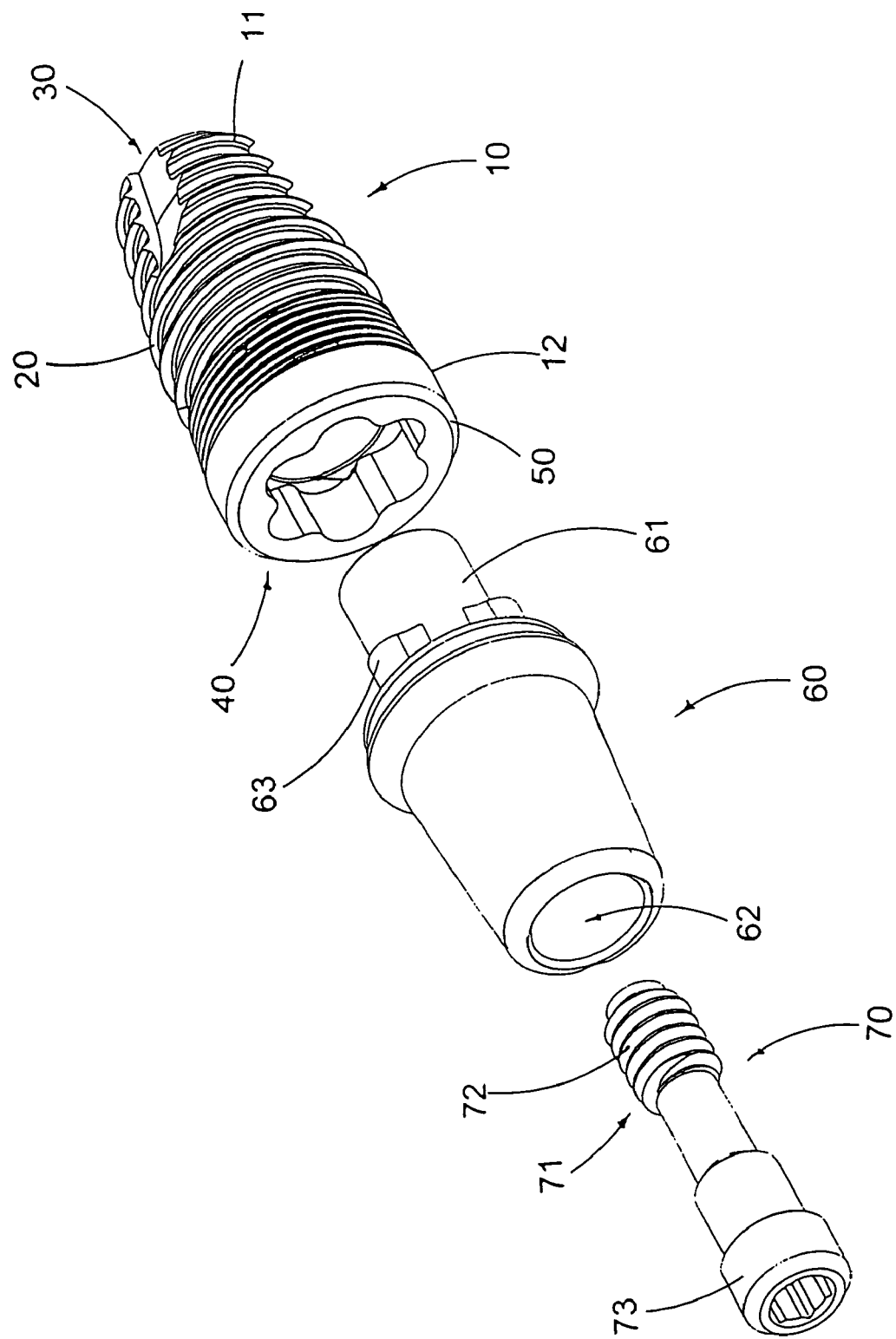
FIG. 2 is an exploded view illustrating a dental implant, an abutment and a bolt for securing the abutment with the dental implant according to above preferred embodiment of the present invention.
Figure 3:
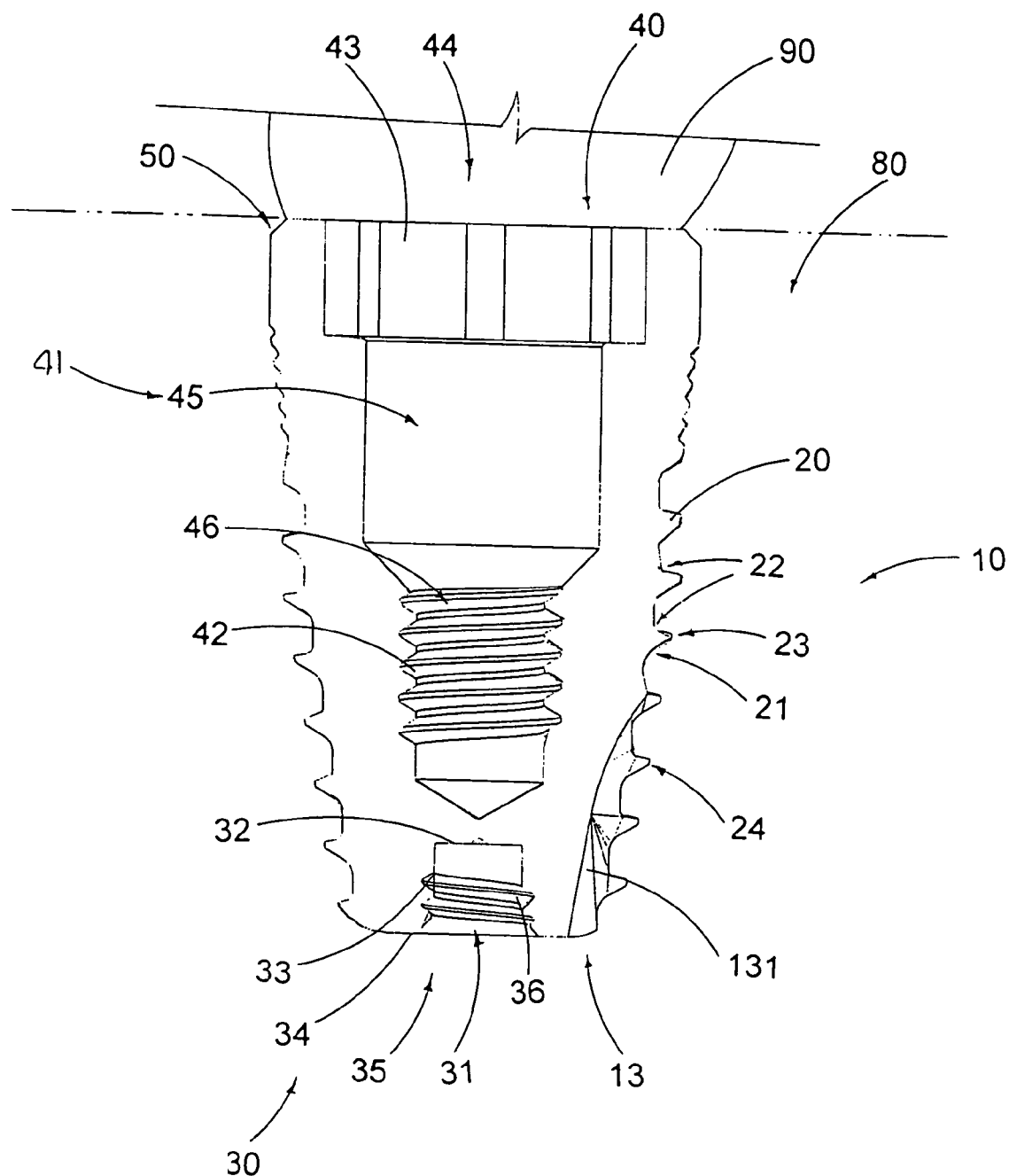
FIG. 3 is a sectional view of the dental implant according to the above preferred embodiment of the present invention.

Referring FIGS. 1 to 3 of the drawings, a dental implant according to a preferred embodiment of the present invention is illustrated, wherein the dental implant comprises a dental implant body 10 which is a cylinder body having a first end 11 for inserting into the sinus of the desired position and a second end 12 for integrally connected with an abutment 60 through a bolt 70, wherein an asymmetric thread 20 is provided around the dental implant body 10, an apex lock 30 is formed at the first end, and an endomaximum lock 40 is provided at the second end.

The dental implant body 10 has a circular cross section extended between the first end 11 and the second end 12 and a tapered insertion root portion adjacent the first end 11, enabling the dental implant to be more easily inserted into the sinus. The second end 12 of the dental implant body 10 is designed to be exposed out of the gum for connecting with abutment 60. The dimension, including the length and the diameter, of the dental implant body 10 varies according to different sinus situation.

The asymmetric thread 20 is integrally formed around an outer wall of the dental implant body 10 and extending from the second end 12 to the first end 11 thereof. The asymmetric thread 20 is a continued thread, or, alternatively discontinued in multiple segments, adapted to screw into the bone of the sinus and be retained by the bone steadfastly.

Referring to FIG. 3, since symmetric thread is not efficient enough for a dental implant, the asymmetric thread 20 of the present invention is made asymmetrical that the two sides of the thread have different slope angles. As illustrated in the cross sectional view of FIG. 3, the asymmetric thread 20 has a first side 21 and a second side 22. The first side, which is facing the first end 11 of the dental implant body 10, has a smaller slope angle while the second side 22, which is facing the second end 12 of the dental implant body 10, has a larger slope angle, so that the second side 22 is more precipitous than the first side 21. Since the slope angle of the first side 21 is smaller, it has less resistance when the dental implant is inserted into the sinus. In contrast, since the slope angle of the second side 22 is larger, it has larger resistance to pull the dental implant out of the sinus. Accordingly, the asymmetric thread 20 is more efficient to be inserted into sinus and increases the stability of the implant after the operation.

According to the hardness, bone can be divided into 4 types. Type 1 represents the hardest bone and Type 4 represents the softest bone. The asymmetric thread 20 also structured to have a blade edge 23 at a tip between the first and second sides 21, 22. The blade edge 23 can acts as self cutting edge which can easily cut into the bone of Types 3 and 4, or has less resistance for bone or Types 1 and 2. When the dental implant is screwed into the sinus where the bone is Type 3 or 4, the sharpened blade edge 23 can cut into the surrounding bone without drilling. It substantially realizes drill-less implant operation. If the bone is Type 1 or 2, much less bone is required to be drilled to insert the dental implant. This will maximally reduce the bone loss which is critical for high stability and successful rate of dental implant. Moreover, the sharpened blade edge 23 of the asymmetric thread 20 also largely reduces the heat generated during screwing, and reduces the time for operation. Both heat and time largely affect the successful rate of operation.

The asymmetric thread 20 comprises an elongated segment of main thread portion 202 and a short segment of end thread portion 201 provided adjacent to the second end 12 while the main thread portion 202 extended immediately from the end thread portion 201 to the first end 11. The end thread portion 14 has lower height and shorter pitch. In other words, the end thread portion 202 has a smaller dimension than the main thread portion 201 because the bone density is decreasing at the apical position than at the coronal position of the jaw. In order to guarantee enough contact area between the end thread portion 202 and the jaw bone for stability, the coronal thread portion 202 increases the number of pitches.

In order to further facilitate the insertion of the dental implant into the sinus, a plurality of apex indentations 13 is spacedly formed in the insertion root portion of the dental implant body 10. Referring to FIGS. 1 to 3 of the drawings, in a preferred embodiment of the present invention, each apex indentation 13 has a V-shape cross section defining two blade surfaces 131 cutting into the dental implant body 10 from the tip of the first end 11 of the dental implant body 10. At these two blade surfaces 131, the cross section of the asymmetric thread 20 is exposed and the blade edge 23 of the asymmetric thread 20 forms one or more cutting blades 24, wherein when the dental implant of the present invention is screwed inside the sinus, the cutting blades 24 are the first part to cut into the bone. If the bone is hard, some bone will be drilled out by the cutting blade 24 but will be reserved inside the indentations 13. In a preferred embodiment, the dental implant body 10 has a total of three apex indentations 13.

Referring to FIG. 3, the apex lock 30 of the dental implant is provided at the first end 11 of the dental implant body. The apex lock 30 has an apex cavity 31 which has a cavity bottom 32 and a cavity wall 33. The cavity wall 33 extends to a periphery edge of the apex lock 30 to form a cavity edge 34. This cavity edge 34 defines an apex opening 35, allowing bone of the sinus to grow into the apex cavity 31.

The apex lock 30 also comprises a lock element 36 in the apex cavity 31. The lock contains grooves or ribs provided around the cavity wall 33 to increase infliction. In a preferred embodiment, the lock element 36 is embodied as an internal thread on the cavity wall 33 of the apex cavity 31. Generally, the bone at the bottom of the sinus gets more blood supply after dental implantation. So at this area the sinus will have better bone growth. The space formed in the apex cavity 31 enables the new grown bone extending into the apex cavity 31 of the apex lock 30 as well as the grooves or the grooves of the internal thread on the cavity wall 33 so as to provide a locking mechanism to ensure the integration between the dental implant and the bone.

One of the issues that cause the failure of dental implantation most often is loosening of the implant. The dental implant could be unscrewed out of the sinus before it is fused tightly with the bone. It is worth mentioning, the internal thread of the cavity wall 33 of the apex cavity 31 is oriented in an opposite direction of the asymmetric thread 20 of the dental implant body 10. In this manner, when extra force is trying to loosening the screw of the asymmetric thread 20, it is also fastening the internal thread of the apex lock 30 at the same time. These two opposite forces will diminish each other. As a result, loosening of the implant after implantation can be avoided.

Figure 4:
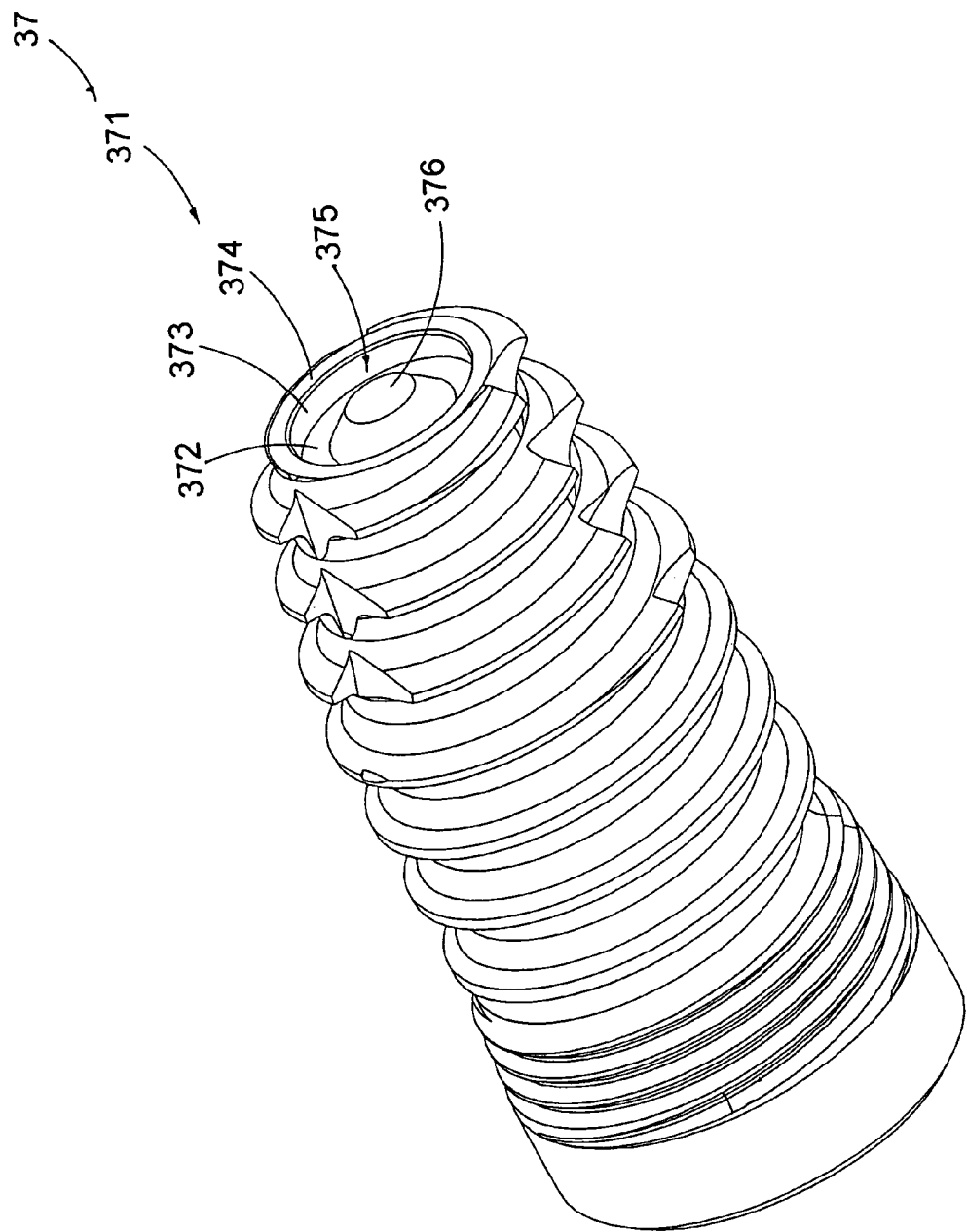
FIG. 4 is a perspective view of an alternative mode of the dental implant according to the above preferred embodiment of the present invention.
Figure 5:
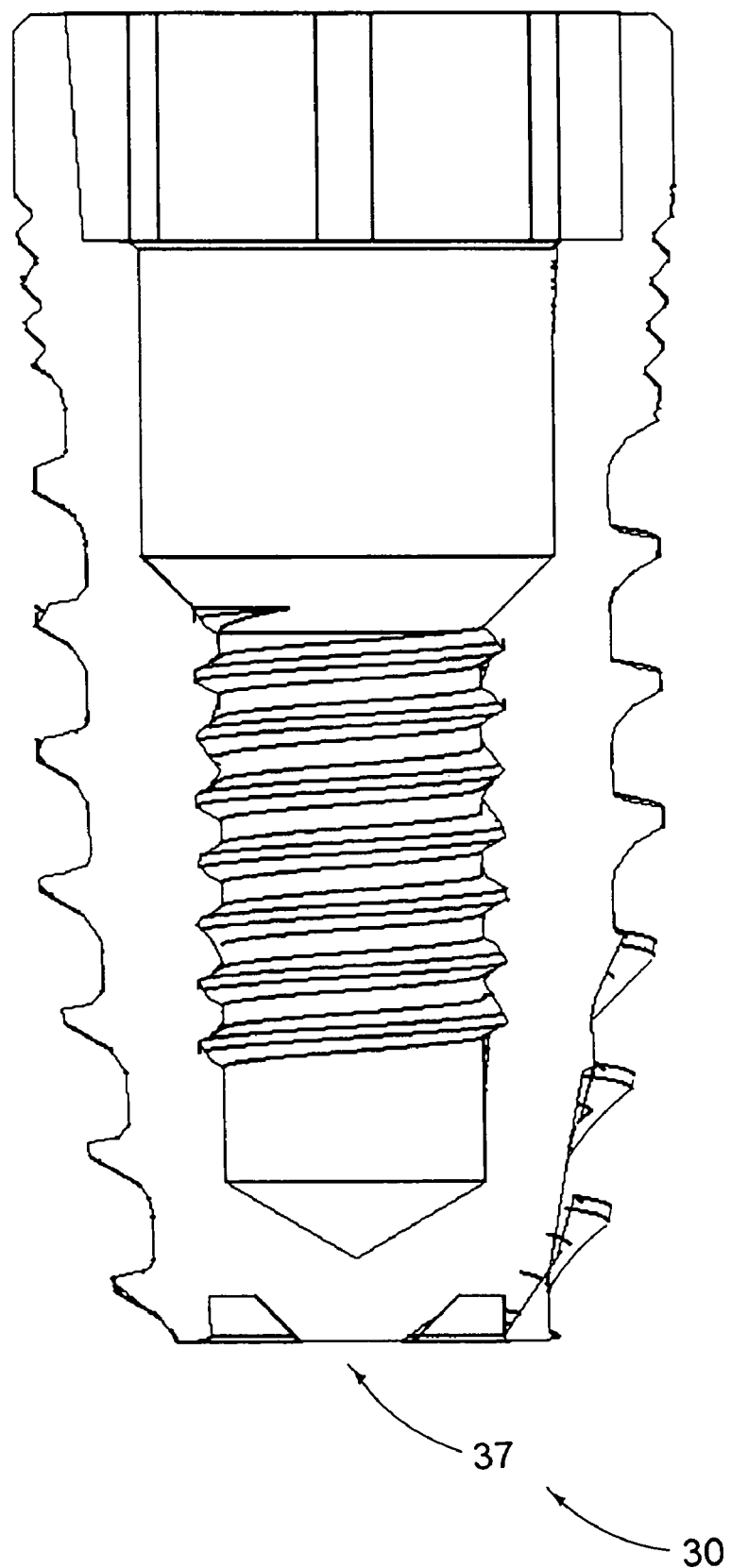
FIG. 5 is a sectional view of the alternative mode of the dental implant according to the above preferred embodiment of the present invention.

In practice, since some sinuses are not very deep, the dental implant can not be too long. In this situation, a shallow apex cavity 31, having no internal thread or only a short internal thread, can be used, where sinus lifting becomes more important. Referring to FIGS. 4 and 5, an alternative mode of the above preferred embodiment according to the present invention is illustrated, wherein the apex lock 30 comprises a trepanelevation tip member 37.

The trepanelevation tip member 37 has a concave tip 371 formed at the first end 11 of the dental implant body 10, which has a concave bottom 372 and a concave wall 373 radially and outwardly extended to a periphery edge of the trepanelevation tip member 37 to form a sharpen tip edge 374 of the concave tip 371. In one embodiment, the concave wall 373 extended from the concave bottom 372 forms a smooth curvature. The concave bottom 372 can be made to have a curve surface or a flat surface. The concave bottom 372 and the concave wall 373 integrally define a cavity 375 at the tip end of the trepanelevation tip member 37.

The trepanelevation tip member 37 also provides a prominence 376 protruded from the concave bottom 372. In a preferred embodiment of the present invention, the prominence 376 is protruded from a central portion of the concave bottom 372. The prominence 376 has a convex shape and a smoothly curved exterior surface. The height of the prominence 376 must be equal or less than the depth of the concave tip 371, so that the prominence 376 does not extend beyond the sharpen tip edge 374. In this manner, the prominence 376 will not be the first portion contacting with the surface of the bone, in order to prevent the trepanelevation tip member 37 from sliding away from the desired position.

When the dental implant with the trepanelevation tip member 37 is screwed into the sinus, the trepanelevation tip member 37 is applied on the floor of the sinus. Because of the asymmetric thread 20, the torque is converted to linear force towards the floor of the sinus. The trepanelevation tip member 37 will perform the bone expansion with the outer wall. At the same time, the trepanelevation tip member 37 is going deeper into the sinus and elevates the sinus floor. Because the trepanelevation tip member 37 has the convex prominence 376, the intention of the pressure is enlarged. This will increase the efficiency to compress the bone material inside the cavity 375 of the trepanelevation tip member 37. With the capability of sinus lifting and bone expansion due to the trepanelevation tip member 37, the dental implant will be retained more stable.

Referring to FIGS. 1 to 3, the endomaximum lock 40 of the dental implant of the present invention is for locking the abutment 60. The endomaximum lock 40 provides a lock cavity 41, a lock thread 42 and a universal holder 43. The lock cavity 41 has a lock opening 44 at the second end 12 of the dental implant body 10, and extends longitudinally inside the dental implant. The lock cavity 41 has two sections. The first section 45 of the lock cavity 41 is close to the lock opening 44. This section is adapted to contain the root 61 of the abutment 60 and the diameter of this section is the same as the root of the abutment 60.

The second section 46 is adjacent to the first section 45 and deeper inside the lock cavity 41. The lock thread 42 is provided around the inner wall of the second section. This lock thread 42 is adapted to be screwed with the bolt 70. After a dental implant is secured inside the sinus, the abutment 60 is ready to be mounted. First, the root of the abutment 60 is inserted into the first section 45 of the lock cavity 41. Then the abutment 60 is fastened onto the dental implant through the bolt 70. The abutment 60 has a through hole 62 communicating the lock opening 44 and the second section of the lock cavity 41. A tip 71 of the bolt 70 having an external thread 72 is adapted to pass through the through hole 62 of the abutment 60 and screw with the lock through of the dental implant. A head 73 of the bolt 70 remains in the through hole 62 of the abutment 60 for driving the bolt 70 and retaining the abutment 60. In this manner, the bolt 70 and the dental implant body 10 have a metal to metal contact which is very stable. This can steadily fasten the abutment 60 onto the dental implant. The stability is largely increased.

Referring to FIGS. 1 to 3, according to the preferred embodiment of the present invention, the endomaximum lock 40 comprises a universal holder 43 having six engaging slots 431 while the abutment 60 has three engaging jaws 63 protruded from root 61 thereof. When the engaging jaws 63 are inserted and engaged in the engaging slots 431 of the dental implant body 10, the rotation of the abutment 60 is secured.

In a preferred embodiment of the present invention, the universal holder 43 is provided at the lock opening 44 of the lock cavity 41 and each of the engaging slots 431 has a curve profile. These six engaging slots 431 are distributed around the axle of the dental implant evenly with an angle of 60° between two adjacent engaging slots 431. The three engaging jaws 63 of the relative abutment 60 have the same profile of the engaging slots 431 and are distributed around the axle of the abutment 60 with an angle of 120° between each other.

It is worth mentioning that the conventional dental implant generally has only three engaging slots for engaging with three engaging jaws of the conventional abutment, wherein the abutment 60 has to be rotated 120° to get to the next secure position and there are only three secured positions to choose. This is very inconvenient to place the abutment with a suitable rotary angle especially when the root of the abutment has an angle. According to the preferred embodiment of the present invention, the universal holder 43 has six engaging slots 431 distributed evenly around the axle of the dental implant. So that the angle is 60° rotating from one engaging slot 431 to the next engaging slot 431 and the abutment 60 has six secured positions to choose while the prior art dental implant merely contains three secured positions to choose. In other words, the prior art dental implant needs to be rotated 120° to find the next secured position and the dental implant of the present invention enables the dentist to simply rotate it for 60° for the next secured position. It is much flexible to find a suitable rotary angle for easy alignment of the dental crown.

Referring to FIGS. 1 to 5, the dental implant body 10 further has a ferroembrace 50 provided around the second end 12 thereof. The ferroembrace 50 is a bevel wall 51 extending inwardly from the periphery edge of the second end 12 of the dental implant body 10. The ferroembrace 50 thickens the second end 12 of the dental implant body 10 while slightly decreases the diameter of the profile. The purpose of the ferroembrace 50 design is for esthetics and retention reasons. If the dental implant is inserted into the sinus too shallow, the metal of the implant body will be exposed which is not esthetical. The ferroembrace 50 of the present invention helps the surgeon to control the depth of the dental implant to be inserted. During the surgery, the gum should be placed on the bevel wall of the ferroembrace 50. In this manner, the gum tissue is healthier and thicker, less metal of the dental implant body 10 is exposed, and the stability of the dental implant is increased. In addition, porcelain margin of a restoration can be used to cover the exposed bevel to improve esthetics and restoration.

In summary, the present invention is a self-drilling and drill-less dental implant. It utilizes asymmetric thread 20 to ease the implant surgery and increase the stability of the integration. The blade edge 23 and the cutting blades 24 of the asymmetric thread 20 maximally preserved the bone during screwing. The apex lock 30 provides the apex cavity 31 so that the bone at the sinus floor can grow into it. The internal thread 36 increases the friction so the bone can integrate with the dental implant in more stable manner. Also the internal thread 36 has an opposite direction of the asymmetric thread 20 which prevents the implant loose. The apex lock 30 can also had a trepanelevation tip member 37 adapted to perform sinus lifting during the operation of dental implantation.

The present invention also provides an endomaximum lock 40 providing metal to metal contact to secure the abutment 60 onto the dental implant body 10. The universal holder 43 provides more slots to increase the flexibility for securing and alignment. The ferroembrace helps the surgeon to control the implant position, retention of restoration and reduces the metal exposure.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A dental implant for inserting into a sinus of a gum, comprising:

a dental implant body which is a cylindrical body having a first end, a second end, a ferroembrace, and an asymmetric thread formed around said dental implant body, wherein said second end is a threadless end portion and said asymmetric thread has an elongated segment of main thread portion and a short segment of end thread portion provided adjacent to said second end portion while said main thread portion extending immediately from said end thread portion to said first end, wherein said main thread portion has a first side, a second side and a blade edge at a tip between said first and second sides, and said end thread portion has lower height and shorter pitch than said main thread portion, so as to form said asymmetric thread, wherein said ferroembrace which is provided around said second of said dental implant body has a bevel wall extending inwardly from a periphery edge of said second end for placing the gum on said bevel wall of said ferroembrace after said dental implant is inserted in the sinus of the gum;

an apex lock formed at said first end of said dental implant body for inserting into the sinus of a desired position, wherein said apex lock has an apex cavity which is a blind hole indented in said first end and has a cavity bottom and a cavity wall extending to a periphery edge of said apex lock, wherein said apex cavity defines an apex opening allowing a new grown bone of the sinus to grow therein, wherein said apex lock comprises a lock element which is an internal thread provided on said cavity wall of said apex cavity for providing a locking mechanism to ensure an integration between said dental implant and the bone of the sinus, wherein said internal thread of said cavity wall of said apex cavity is oriented in an opposite direction of said asymmetric thread, thereby when a force is applied to loosening said asymmetric thread, said internal thread of said apex lock is fastened at the same time; and an endomaximum lock provided at said second end of said implant body for integrally connecting with an abutment through a bolt;

wherein said end thread portion of said asymmetric thread of said dental implant body has a smaller dimension than said main thread portion for increasing contact area between said end thread portion and a surrounding bone of the sinus for stability;

wherein said first side of said main thread portion of said asymmetric thread, which is facing the first end of said dental implant body, has a smaller slope angle while said second side of said main thread portion of said asymmetric thread, which is facing said second end of said dental implant body, has a larger slope angle, rendering said second side being more precipitous than said first side, thereby said first side with smaller slope angle reduces resistance when said dental implant is inserted into said sinus, and said second side with larger slope angle increases resistance to pull said dental implant out of said sinus so as to increases a stability of said dental implant after inserted into said sinus;

wherein said blade edge is a self-cutting edge for cutting into the surrounding bone of the sinus without drilling out the surrounding bone of the sinus for maximally reducing bone loss during the inserting of said dental implant into the sinus;

wherein said main thread portion of said dental implant body has a tapered insertion root portion adjacent said first end thereof and a plurality of apex indentions spacedly formed in said insertion root portion of said dental implant body, wherein each said apex indention has a V-shape cross section defining two blade surfaces cutting into said dental implant body from a tip of said first end of said dental implant body, wherein at said two blade surfaces, said blade edge forms one or more cutting blades, thereby when said dental implant is screwed inside the sinus, said cutting blades cut into the surrounding bone of the sinus first and any surrounding bone drilled out by said cutting blades is reserved inside said apex indentations.

2. The dental implant, as recited in claim 1, wherein said endomaximum lock has a lock cavity and a universal holder, wherein said lock cavity has a lock opening formed at said second end for receiving a root of said abutment therein, and said universal holder has a plurality of engaging slots formed at said lock opening adapted for respective engaging jaws protruded from the root of the abutment to engage.

3. The dental implant, as recited in claim 2, wherein said engaging slots are distributed evenly around an axle of said dental implant body.

4. The dental implant, as recited in claim 3, wherein six engaging slots are provided with an angle of 60° between said two adjacent engaging slots for engaging with three engaging jaws of the abutment.

5. The dental implant, as recited in claim 2, wherein said lock cavity has a first section and a second section, wherein said first section is positioned closer to said locking opening for containing the root of the abutment and has a diameter the same as the root of the abutment, wherein said second section is adjacent to said first section and deeper inside said lock cavity.

6. The dental implant, as recited in claim 3, wherein said lock cavity has a first section and a second section, wherein said first section is positioned closer to said locking opening for containing the root of the abutment and has a diameter the same as the root of the abutment, wherein said second section is adjacent to said first section and deeper inside said lock cavity.

7. The dental implant, as recited in claim 4, wherein said lock cavity has a first section and a second section, wherein said first section is positioned closer to said locking opening for containing the root of the abutment and has a diameter the same as the root of the abutment, wherein said second section is adjacent to said first section and deeper inside said lock cavity.

8. The dental implant, as recited in claim 2, wherein said second section of said lock cavity has a lock thread provided around an inner wall of said second section for screwing with the bolt.

9. The dental implant, as recited in claim 3, wherein said second section of said lock cavity has a lock thread provided around an inner wall of said second section for screwing with the bolt.

10. The dental implant, as recited in claim 4, wherein said second section of said lock cavity has a lock thread provided around an inner wall of said second section for screwing with the bolt.

11. The dental implant, as recited in claim 5, wherein said second section of said lock cavity has a lock thread provided around an inner wall of said second section for screwing with the bolt.

12. The dental implant, as recited in claim 6, wherein said second section of said lock cavity has a lock thread provided around an inner wall of said second section for screwing with the bolt.

13. The dental implant, as recited in claim 7, wherein said second section of said lock cavity has a lock thread provided around an inner wall of said second section for screwing with the bolt.

* * * * *